United States Patent [19]

Krigmont et al.

[11] Patent Number: 5,008,628
[45] Date of Patent: Apr. 16, 1991

[54] MEASUREMENT OF ELECTRICAL RESISTIVITY OF PARTICULATE ENTRAINED IN A GAS STREAM

[75] Inventors: Henry V. Krigmont, Seal Beach; Everett L. Coe, Jr., Downey, both of Calif.

[73] Assignee: Wahlco, Inc., Santa Ana, Calif.

[21] Appl. No.: 361,273

[22] Filed: Jun. 5, 1989

[51] Int. Cl.⁵ ............................................ G01R 27/02
[52] U.S. Cl. .................................... 324/693; 324/715; 324/716; 324/724; 324/464; 304/627; 73/28.01
[58] Field of Search ............... 324/693, 699, 713, 715, 324/716, 717, 724, 444, 446, 448, 449, 450, 464, 466; 340/627, 628; 55/18; 73/28.01

[56] References Cited
U.S. PATENT DOCUMENTS

| | | | |
|---|---|---|---|
| 3,515,987 | 6/1970 | Zurbrick et al. | 324/688 X |
| 3,686,926 | 8/1972 | Miller et al. | 324/717 X |
| 4,656,832 | 4/1987 | Yukihisa et al. | 324/717 X |

OTHER PUBLICATIONS

Grady B. Nichols, "Techniques for Measuring Fly Ash Resistivity", Enviromental Protection Agency Publication EPA–650/2–74–079, pp. 1–41 (Aug. 1974).

Primary Examiner—Reinhard J. Eisenzopf
Assistant Examiner—Jack B. Harvey
Attorney, Agent, or Firm—Howard E. Sandler; Gregory O. Garmong

[57] ABSTRACT

The resistivity of particulate matter in a gas stream, such as a combustion gas stream produced in a coal-fired power plant, is measured by collecting a sample of the particulate on the surface of a porous ceramic cylinder, either with or without an applied collection voltage, and then determining the resistance of the sample with a compound measurement electrode having multiple conductors. The reference electrode and the measurement electrode are spirally wound on the ceramic cylinder in an interdigitated manner, so that the two are laterally adjacent down the length of the cylinder. The pressure within the cylinder is controllable, with a pressure below atmospheric being applied to draw the particulate to the suface and ascertain when a sufficient sample for measurement is present, and a pressure above atmospheric being applied to blow away the sample after the measurement is completed, thereby preparing the instrument for the taking of another sample.

16 Claims, 4 Drawing Sheets

MEASUREMENT OF ELECTRICAL RESISTIVITY OF PARTICULATE ENTRAINED IN A GAS STREAM

BACKGROUND OF THE INVENTION

This invention relates to the measurement of the electrical resistivity of particulate material entrained in gas streams, and, more particularly, to the measurement of the electrical resistivity of the entrained particulate material in power plant combustion gases that are to be subjected to electrostatic precipitation treatment.

In a coal-fired power plant, coal is burned to heat air, which in turn boils water to form steam. The steam drives a turbine and thence an electric generator, producing electricity. Besides heat, the burning of the coal produces gaseous pollutants such as sulfur and nitrogen oxides, and a solid particulate known as fly ash. Environmental protection laws mandate that the amounts of gaseous pollutants and solid particulate emitted from the power plant be maintained at acceptably low levels, and the present invention deals generally with the technology for controlling particulate emissions.

One widely used approach for removing the particulate fly ash from combustion gas streams is electrostatic precipitation. The combustion gas stream with entrained particulate is passed between highly charged electrodes that ionize the particles so that they are attracted to, and deposited upon, a collection electrode. The particulate may optionally be charged prior to entry into the precipitator to increase the efficiency of removal. The cleaned combustion gases are released to the atmosphere, and the precipitated particulate is removed from the collection electrode.

The efficiency of operation of electrostatic precipitators depends markedly upon the electrical resistivity of the particulate. If the resistivity is too high, a collection current cannot be induced to flow between the electrodes of the precipitator, so that the ability to collect particulate is reduced, sometimes severely so. There exist conditioning procedures and apparatus for altering the conductivity of the particulate by injection of conditioning agents into the combustion gas stream prior to its entering the electrostatic precipitator.

An example of such a treatment procedure is that disclosed in U.S. Pat. No. 3,993,429, and this approach has become widely accepted and used throughout the United States and the world. In this approach, a conditioning gas such as sulfur trioxide or ammonia is injected into the combustion gas stream. In the case of sulfur trioxide, the conditioning gas reacts with water in the gas stream to produce sulfuric acid that is deposited upon the surface of the particulate. The ionized sulfuric acid reduces the electrical resistance of the particulate, which in turn raises the electrical conductivity of the fly ash particulate so that the electrostatic precipitation treatment works well. Conditioning treatments are routinely used where the sulfur content of the coal burned in the power plant is so low that the electrical resistivity of the resulting particulate is too high to permit the electrostatic precipitators to operate properly.

The proper amount of conditioning gas to inject, and the best operating settings of the precipitators, must be determined to permit optimum operation of the system. To achieve operating control of the precipitator and/or the conditioning system, it is desirable to know the electrical resistivity of the particulate being precipitated on an ongoing basis, using measurements within the apparatus. With this knowledge, the operation of the system can be optimized in real time under manual or automatic control. If the resistivity of the particulate is not known, then the proper operating parameters can only be approximated, based upon the experience of the operator.

There have been developed various types of apparatus for measuring the electrical resistivity of the particulate. These include the Southern Research Institute point-to-plane probe, the Wahlco cyclonic probe, and the interlocking comb probe. All of these probes permit measurement of some resistivity parameter, but all also suffer from certain shortcomings. The objective of the measurement is to determine the resistivity of the particulate under as realistic conditions as possible, simulating the conditions within the electrostatic precipitator. None of the known types of probes collect truly representative samples of the particulate under the conditions of precipitation. Moreover, none of the known apparatus are continuous or semicontinuous in operation, and must be inserted into the flowing gas stream on an intermittent basis to accomplish the measurement.

There therefore exists a need for an improved apparatus and method for collecting samples and measuring the resistivity of particulate entrained in a gas stream, in a wide variety of circumstances. This need is particularly acute for the measurement of the resistivity of fly ash particulate in the combustion gas stream of coal-fired power plants. Such an approach desirably would collect a representative sample of particulate under precipitator operating conditions. Also, the approach should permit continuous or nearly continuous measurement of resistivity, to allow real-time, continuous control of the gas cleanup system, where present. The present invention fulfills this need, and further provides related advantages.

SUMMARY OF THE INVENTION

The present invention provides an apparatus (also termed a measurement probe or probe) and method for conducting measurements of the electrical resistivity of samples of particulate obtained from flowing gas streams in which the particulate is entrained. The apparatus obtains samples of the particulate that are highly representative of the actual particulate mass on the collection plates of the electrostatic precipitator, because the samples are gathered under conditions approximating those of the precipitator operation. The apparatus is automatic and semi-continuous.

In accordance with the invention, particulate resistivity measurement apparatus comprises a hollow cylindrical substrate made of an electrical insulator; two interdigitated electrodes spirally wound on the substrate, including a measurement electrode, and a reference electrode; a measurement power supply that applies a measurement voltage between the measurement electrode and the reference electrode; and a current measurement meter that measures the current flowing between the measurement electrode and the reference electrode due to the applied measurement voltage.

More specifically, particulate resistivity measurement apparatus comprises a substrate; two adjacently positioned electrodes supported on the substrate, including a measurement electrode having a composite structure including a measurement conductor, a pair of confinement conductors, one on either side of the measurement conductor, and an insulation layer between each of the confinement conductors and the measurement conductor, and a reference electrode; a measurement power supply that applies a measurement voltage between the reference electrode and the measurement conductor of the measurement electrode; and a current measurement meter that measures the current flowing between the reference electrode and the measurement electrode due to the applied measurement voltage.

In a particularly preferred approach, particulate resistivity measurement apparatus, comprises a cylindrical substrate that is sealed at the ends to permit control of the interior pressure of the substrate, and is made of a porous ceramic; a pressure controller communicating with the interior of the substrate, the pressure controller including a vacuum source of a pressure below atmospheric, a purging source of a pressure above atmospheric, and a valve that is controllable to connect the interior of the substrate to either the vacuum source or the purging source; a perforated shield around the exterior of the substrate; two interdigitated electrodes spirally wound on the substrate, including a measurement electrode having a composite structure including a measurement conductor, a pair of confinement conductors, one at a greater cylindrical radius and one at a lesser cylindrical radius than the measurement conductor, and an insulation layer between each of the confinement conductors and the measurement conductor, each of the confinement conductors being at ground potential, and a reference electrode; a measurement power supply that applies a measurement voltage between the reference electrode and the measurement conductor of the measurement electrode; and a current measurement meter that measures the current flowing between the reference electrode and the measurement conductor due to the applied measurement voltage.

In the preferred approach, the measurement electrode and the reference electrode are spirally wound in an interdigitated fashion on the substrate. The confinement conductors and the measurement conductors are grounded, and the confinement conductors minimize extraneous influences on the resistivity measurement. A voltage is applied between the reference electrode and the measurement conductor. The current that flows as a result of the applied voltage provides a measure of the resistivity of the particulate in the gap between the measurement electrode and the reference electrode.

This apparatus is operated in a semi-continuous manner. A sample is collected by drawing a partial vacuum on the porous ceramic cylinder or cup to draw a sample of particulate into the gap between the measurement electrode and the reference electrode. In an important variation of this collection approach that can be employed as appropriate, a conducting shield is positioned around the cylindrical substrate, and a collection voltage applied between the shield and the substrate. The particulate is ionized as it enters the apparatus. The ionized particulate is then both drawn toward the substrate by the gas flow and also propelled toward the substrate by electrostatic force. When a sufficient sample is taken, the gas flow through the ceramic slows to a calibrated level and the collection voltage, if any, is discontinued. A measurement of resistivity is taken by applying the external measurement voltage between the reference electrode and the measurement conductor portion of the measurement electrode.

Because they are otherwise insulated from each other, a current can flow between the reference electrode and the measurement electrode only through the particulate. From a measurement of the current flowing through the particulate, the resistivity is calculated, or, equivalently, a calibration of the measured current to the optimal operating parameters of the electrostatic precipitator and/or conditioning system is made. When the measurement is complete, the pressure on the interior of the porous ceramic cylinder is reversed, and the collected particulate sample is blown away by the flow of gas out through the pores of the ceramic. The apparatus is ready to repeat the measurement by taking a new sample of the particulate.

The invention also encompasses the process for accomplishing the measurement using the apparatus, as described. Generally, a process for performing a resistivity measurement of a particulate entrained in a moving gas stream of combustion gas to be subjected to an electrostatic precipitation process, comprises the steps of collecting a sample of the particulate such that the particles enter the sample under substantially the same kinetic movement conditions as found in the moving gas stream; and measuring the electrical resistance of the sample.

This apparatus and process are an advance in the operation of power plant gas cleanup procedures, providing an automated, semi-continuous measurement of electrical resistivity of particulate in the combustion gas stream. The measurement is reproducible, because the placement of the apparatus is constant and the conditions of sample collection are uniform from test to test. The apparatus has no moving parts within the gas stream, and is reliable to operate. It is no more costly than other types of resistivity measurement devices, and less expensive than some. Other features of the invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENT

Figure 1:
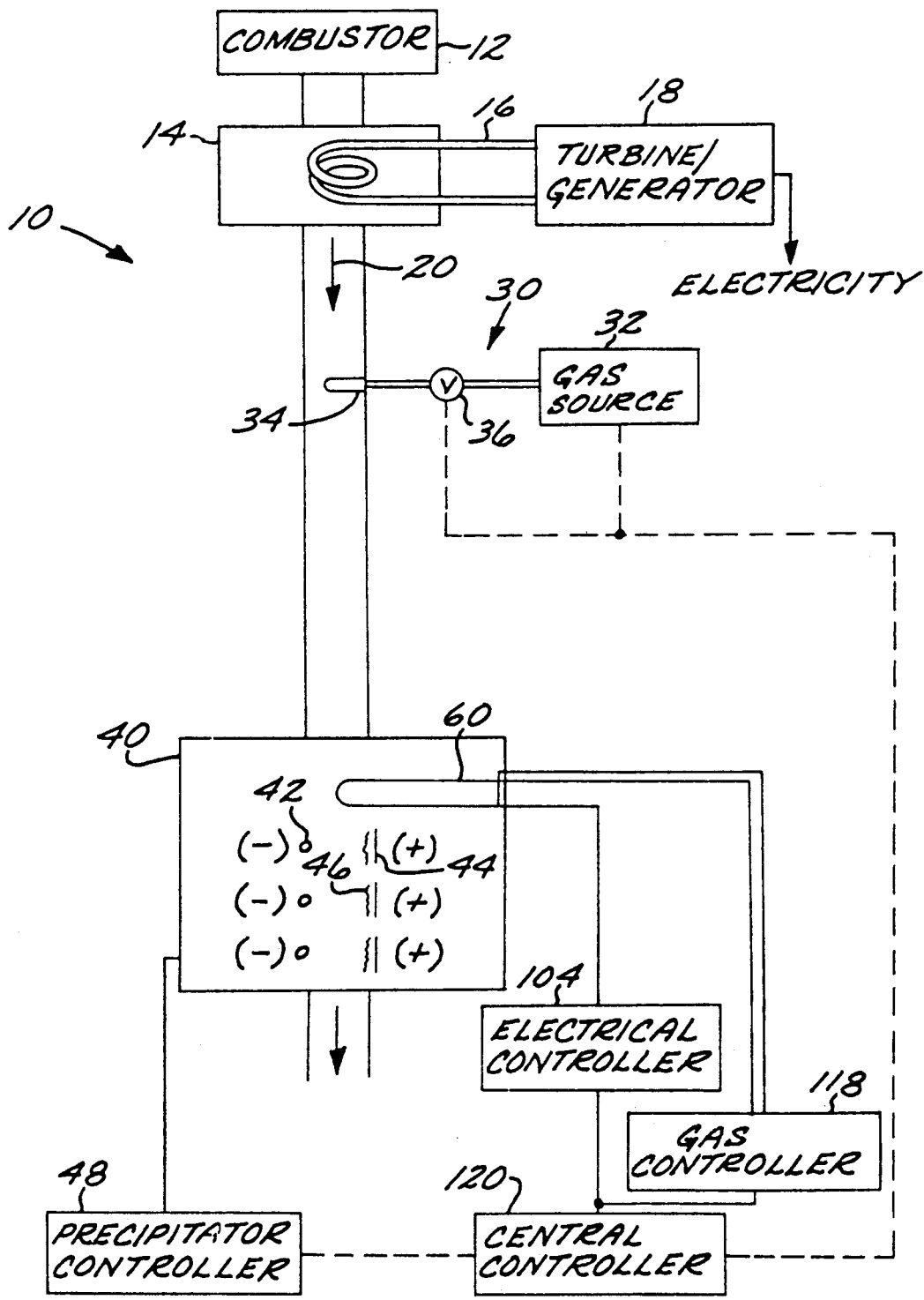
FIG. 1 is a schematic drawing of a power plant combustion gas cleanup apparatus.

The present invention is preferably used in conjunction with an apparatus 10 for precipitating particulate from a combustion gas stream, which is depicted in FIG. 1. In a conventional coal-fired power plant, coal is burned by a combustor 12, and the resulting hot combustion gas is passed through a boiler 14, where it heats and boils water. The resulting steam in a loop 16 flows to a turbine/generator set 18, where electricity for consumption is produced. The steam is condensed, and the water flows back through the loop 16.

The combustion gas stream leaving the boiler 14, indicated by numeral 20, cannot normally be exhausted directly to the atmosphere, because it contains the particulate or fly ash resulting from the combustion 12. If it were exhausted to the atmosphere, the fly ash would deposit on everything surrounding the power plant, leaving a thick coating of soot. Fortunately, the fly ash can be removed from the combustion gas stream 20 by electrostatic precipitator technology, if the fly ash has a sufficiently low electrical resistivity.

The fly ash produced by some types of coal, particularly coal containing a low sulfur content, has too high an electrical resistance to be processed in an electrostatic precipitator, and therefore must be conditioned before entering the precipitator. It is known to inject a conditioning gas into the combustion gas stream by a conditioning apparatus 30, illustrated schematically in FIG. 1.

The conditioning apparatus 30 injects a conditioning agent (that may be a gas, a liquid, or a solid, but is preferably a gas) into the combustion gas stream 20. The conditioning agent is preferably sulfur trioxide, but may be, for example, other gaseous oxides of sulfur, ammonia, or water vapor. The preferred apparatus 30 therefore includes a source 32 of the conditioning gas, and a plurality of injector nozzles 34 that extend into the combustion gas stream 20 to inject the conditioning gas directly into the stream 20. A valve 36, or other flow control device, meters the conditioning gas into the combustion gas stream 20 through the nozzles 34. A preferred source 32 is disclosed in U.S. Pat. No. 3,993,429, and a preferred construction of the nozzles 34 is disclosed in U.S. Pat. No. 4,179,071. The disclosures of both of these patents are incorporated herein by reference.

The injected conditioning gas molecules react with the particulate in the gas stream to increase the conductivity of the particulate, or, alternatively stated, to lower its resistivity. In the case of the preferred sulfur trioxide conditioning gas, the conditioning gas reacts with the residual moisture in the combustion gas to form sulfuric acid on the surface of the particulate, which increases the electrical conductivity of the particulate.

After conditioning, if any, of the combustion gas stream 20, the combustion gas flows to an electrostatic precipitator 40. The precipitator 40 may be of any of the many types commercially available and known in the art. The precipitator 40 includes a plurality of electrodes 42 charged with a high voltage, and grounded precipitation plates 44. The particulate in the gas stream 20 is ionized by the electrostatic field established between the electrodes 42 and the plates 44, and is attracted to be deposited as a layer 46 upon the plates 44 for subsequent removal. The operation of the electrostatic precipitator 40, including the voltage and current applied to the electrodes 42, the rapping of the plates 44 to cause the collected particulate to fall into hoppers, and auxiliary control and display functions are under the control of an electrostatic precipitator controller 48.

To operate the source 32, the valve 36, and the controller 48 in an optimal manner, it is necessary to assess the electrical resistivity of the particulate being deposited as the layer 46 in the electrostatic precipitator 40.

The present invention provides measurement apparatus for that purpose.

A particulate resistivity measurement apparatus 60 is mounted within or upstream of (closer to the combustor 12) the electrostatic precipitator 40. The apparatus 60 provides a semi-continuous measurement of the resistivity of the particulate deposited under conditions similar to those experienced by the layer 46 in the precipitator.

Figure 2:
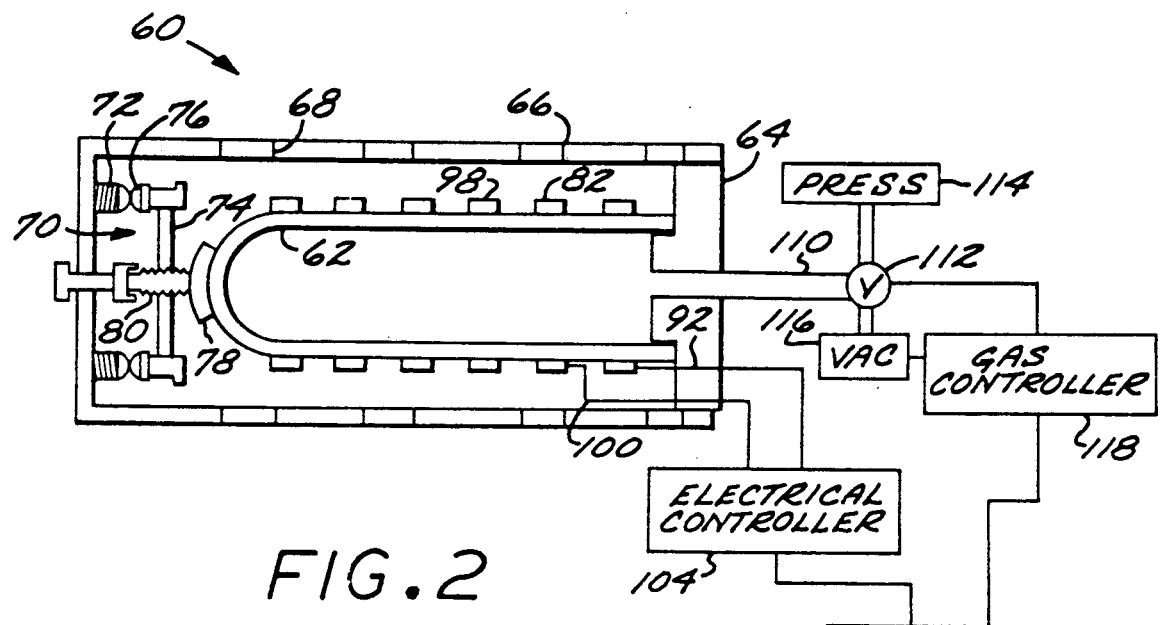
FIG. 2 is a schematic side sectional view of one embodiment of an apparatus for measuring resistivity, with associated equipment and instrumentation shown pictorially.
Figure 3:
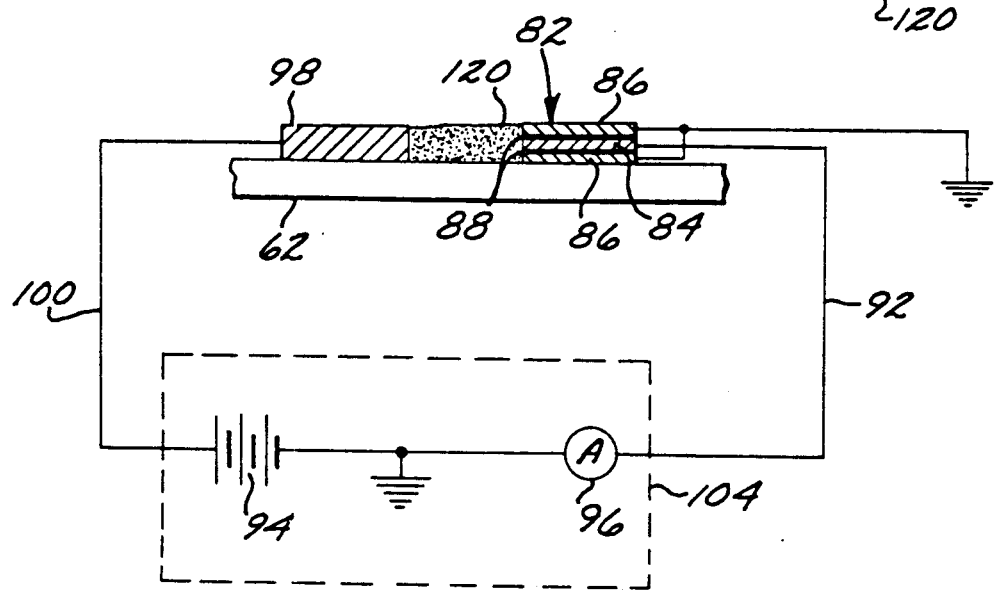
FIG. 3 is an enlargement of a detail of FIG. 2, illustrating the structure and interrelationship of the electrodes.

Referring to FIGS. 2 and 3, the apparatus 60 includes a porous cylinder 62 that is closed at one end. This cylinder 62 is also variously referred to as a cup or thimble. The cylinder 62 is preferably a ceramic such as aluminum oxide, but may be a glass, a high temperature plastic, or other suitable material. The cylinder 62 should have a reasonably low coefficient of thermal expansion and must be structurally sound but porous to the passage of pressurized gas. Such cylinders are readily available as 35–47 percent dense aluminum oxide closed-one-end cylinders from Norton Co. The cylinder 62 is mounted to a fitting 64.

Also mounted to the fitting 64 is a shield 66 that has a plurality of perforations 68 or holes therethrough to admit the particulate-laden gas, bearing its entrained particulate, to the interior of the shield 66 and to the outer surface of the cylinder 62. (An unperforated shield with an entry port, such as will be discussed in relation to the embodiment of FIG. 7, can also be used.) The distal end of the shield 66 is closed, and supports a pressure clamp 70 that holds the cylinder 62 in place against the fitting 64. The pressure clamp includes a pair of posts 72 that support a cross piece 74. The cross piece 74 is preferably flexible, and is mounted to the posts 72 using expansion washers 76 that permit the shield 66 to expand with increasing temperature while still retaining pressure against the closed end of the cylinder 62 through a pressure pad 78. The pressure pad 78 is mounted to the cross piece 74 with a compression screw 80 that may be tightened or loosened to adjust the retaining pressure against the end of the cylinder 62. This arrangement provides a reliable, adjustable approach for mounting the elements of the apparatus 60 together.

Wrapped around the outer circumference of the cylinder 62 in an interdigitated, spirally wound configuration are two electrodes, whose structure and relationship are depicted in more detail in FIG. 3. A measurement electrode 82 has a compsite structure with a single measurement conductor 84 sandwiched between two confinement conductors 86. An insulation layer 88 separates the measurement conductor 84 from each of the confinement conductors 86 on either side. The two confinement conductors 86 are grounded.

A reference electrode 98 is a solid electrical conductor that is spirally wound around the cylinder 62 in an interdigitated fashion with the measurement electrode 82.

The reference electrode 98 is connected through a lead 100 to the high side of a measurement power supply 94. The low side of the power supply 94 is grounded, but connected to the measurement conductor 84 of the measurement electrode 82 through a lead 92. The power supply 94 applies a voltage, for example 1,000 volts, between the reference electrode 98 and the measurement conductor 84. If the gap between the reference electrode 98 and the measurement conductor 84 is filled with an electrically conducting material, depicted as a conducting particulate mass 102, a current flows. The current flowing under this impressed voltage is measured by an ammeter 96 in the circuit. This current is a direct measure of the resistivity of the particulate material in the gap.

The power supply 94 and the ammeter 96 are typically packaged together as an electrical controller 104.

The preceding discussion has dealt with the manner of making the electrical resistivity measurement, after a particulate mass 102 has been collected between the electrodes 82 and 98. The following discussion deals with the collection of the sample of particulate and its disposal after the resistivity measurement has been completed.

A gas line 110 communicates with the interior of the cylinder 62 through an opening in the fitting 64. The gas line 110 connects externally to a three-way valve 112. The valve 112 can be operated to connect the interior of the cylinder 62 to a pressure source 114 or a vacuum source 116. The valve is controlled by a gas controller 118.

The electrical controller 104 and the gas controller 118 are both under the control of a central controller 120. The controller 120 establishes a sequence of operation of the electrical voltages in the controller 104 and the pressure or evacuation instructions in the controller 118. It also monitors the current measured by the ammeter 96, which is an indication of the resistivity and thence the nature of the particulate being measured. This latter information is used by a human operator or a computer that has been programmed with an algorithm which relates operation of the precipitator and conditioning apparatus to particulate conductivity. When operated in an automatic mode, the controller 120 can send command signals to the electrostatic precipitation controller 48, the valve 36, and the source 32.

Figure 4:
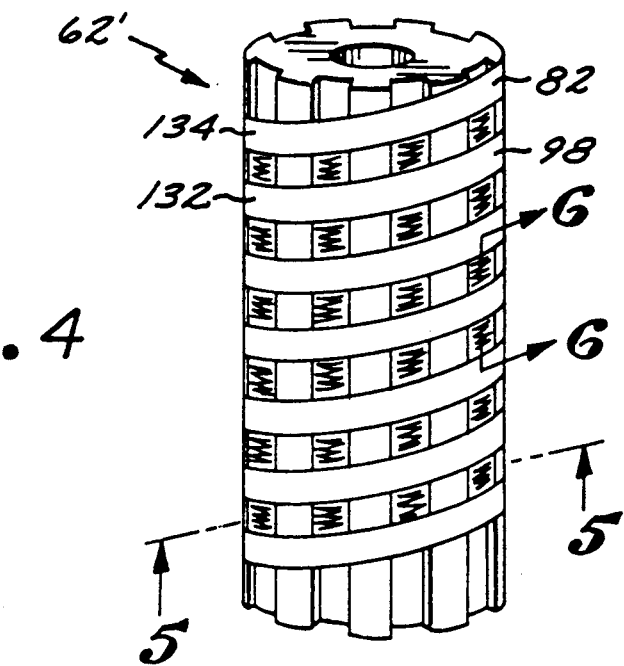
FIG. 4 is a perspective view of one construction for the porous cylinder used to collect the particulate.
Figure 5:
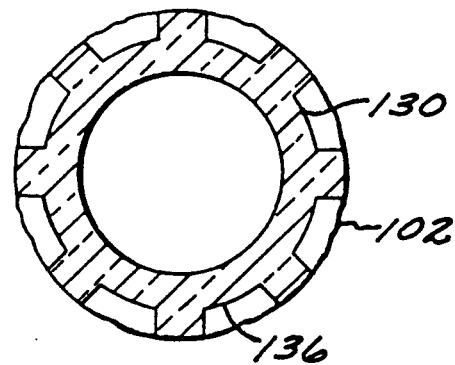
FIG. 5 is a sectional view of the cylinder of FIG. 4 transverse to the cylindrical axis, taken generally along lines 5—5.
Figure 6:
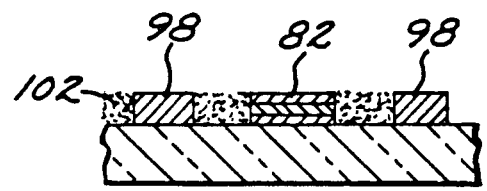
FIG. 6 is a sectional view of the cylinder of FIG. 4 transverse to the radius of the cylinder, taken generally along lines 6—6.

A particularly preferred construction of the cylinder 62 is illustrated in FIGS. 4-6. The cylinder 62 could be formed with a smooth outer wall, but such construction might permit the electrodes 82 and 98 to shift in position with repeated expansion and contraction during temperature cycling. A cylinder 62' has a plurality of longitudinal grooves 130 in its outer periphery extending parallel to the axis of the cylinder. There are also two interdigitated spirally wrapped grooves 132 and 134 in the outer periphery.

The reference electrode 98 is wound spirally around the cylinder 62' in one of the spiral grooves, here the groove 132. The measurement electrode 82 is wound spirally around the cylinder 62' in the other spiral groove, here the groove 134. The placement of the electrodes in the grooves prevents significant shifts of position that might produce questionable resistivity results. The particulate mass 102 is collected in the portion, here indicated by the numeral 136, of the longitudinal grooves 130 that is between the supporting structure. The particulate sample is reproducible both in amount and placement between the electrodes 82 and 98, ensuring reproducible results.

The apparatus 60 functions in the following manner. The gas controller 118 is operated to draw a mild vacuum on the interior of the cylinder 62 by connecting the gas line 110 to the vacuum source 116 through the valve 112. Combustion (or other) gas with entrained particulate flows through the perforations 68 of the shield 66, and the particulate mass 102 is deposited upon the outer surface of the cylinder 62 between and over the electrodes 82 and 98. The gas flow through the vacuum source 116 is initially rapid, because there is little resistance other than the resistance offered by the porous ceramic of the cylinder 62. As the particulate layer grows in thickness, the flow decreases because of the flow resistance offered by the mass of particulate 102. When the flow resistance increases to a calibrated amount, the controller 120 determines that a sufficient mass 102 is present to conduct a measurement.

To this point of the cycle, the measurement power supply 94 is not operating. When the mass 102 is of sufficient thickness, the power supply 94 is operated to apply the measurement voltage between the reference conductor 98 and the measurement conductor 84 of the measurement electrode 82. The only current path to complete the circuit is through the accumulated particulate mass 102, and the current measured by the ammeter 96 is inversely related to the resistance of the mass 102. In this manner, the electrical resistance of the particulate in the mass 102 is determined. This resistance can then be related to electrical resistivity or simply compared to calibration standards to determine the operation of the precipitator and/or the conditioning gas supply.

After the measurement is complete, the gas controller 118 is operated to connect the gas line 110 to the pressure source 114 through the valve 112, pressurizing the interior of the cylinder 62. The accumulated mass 102 is blown away by the gas escaping through the pores of the cylinder 62. The apparatus 60 is then ready for another measurement.

Figure 7:
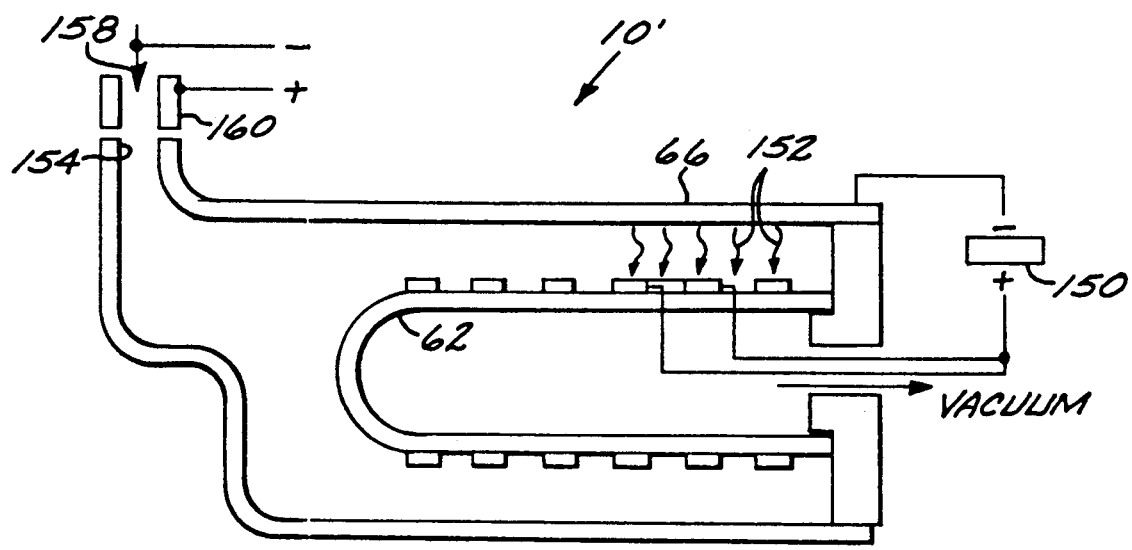
FIG. 7 is a schematic side sectional view of a second embodiment of an apparatus for measuring resistivity.

Another embodiment of the measurement apparatus 10' is illustrated in FIG. 7. The cylinder 62, electrodes 82 and 98, gas flow system, and electrical resistance circuitry for this embodiment are identical to those discussed previously. The difference resides in the mode of collection of the particulate sample. There are two driving forces for the collection in the embodiment of FIG. 7. One is the gas inflow through the porous wall of the cylinder 62, as discussed previously.

The other is an electrostatic driving force that simulates the electrostatic compaction forces produced between the electrode 42 and the plate 44 of the electrostatic precipitator 40. Simulating the electrostatic compaction force may be important, because the resistivity of the particulate mass 102 may be dependent upon the extent of compaction.

To simulate the electrostatic compaction force, the shield 66 is made of a conducting solid such as a metal. The shield 66 is charged electrostatically with respect to the electrodes 82 and 98 during the sample collection period, using a collection power supply 150. If the particulate particles are ionized, they are driven inwardly toward the cylinder 62 with an electrostatic driving force, as indicated schematically by arrows 152. The compaction voltage between the shield 66, on the one hand, and the electrodes 82 and 98, on the other, is typically sufficient to produce a voltage of 4 to 5 kilovolts per inch of separation between the shield 66 and the cylinder 62, but may be adjusted to optimally simulate the behavior of the precipitator 40.

The gas-entrained particulate enters the apparatus 10' through a port 154. As the particulate enters the apparatus, it passes between oppositely charged electrodes 158 and 160, which have a voltage typically of about 4–5 kilovolts per inch of separation between them. The particles in the gas stream are ionized, so that they may be electrostatically accelerated from the shield 66 to the cylinder 62, as well as being drawn toward the cylinder 62 by the flowing gas stream under the influence of the partial vacuum applied to the interior of the cylinder.

The present apparatus and process thus provide a probe for measuring the properties of particulate that is deposited under conditions similar to those in the electrostatic precipitator. Although a particular embodiment of the invention has been described in detail for purposes of illustration, various modifications may be made without departing from the spirit and scope of the invention. Accordingly, the invention is not to be limited except as by the appended claims.

What is claimed is:

1. Particulate resistivity measurement apparatus, comprising:
   a substrate having a first side and a second side;
   two adjacently positioned electrodes supported on the first side of the substrate, including
      a measurement electrode, and
      a reference electrode;
   means for applying a vacuum to the second side of the substrate to controllably draw gas through the substrate so that particulate matter carried by the gas is deposited on the first side of the substrate;
   a measurement power supply that applies a measurement voltage between the reference electrode and the measurement electrode; and
   a current measurement meter that measures the current flowing between the reference electrode and the measurement electrode due to the applied measurement voltage.

2. The apparatus of claim 1, wherein the substrate is cylindrical in shape.

3. The apparatus of claim 2, wherein the measurement electrode and the reference electrode are spirally wound in an interdigitated fashion on the substrate.

4. The apparatus of claim 1, further including a shield around the substrate.

5. The apparatus of claim 4, further including a collection power supply that applies a collection voltage between the shield, on the one hand, and the reference electrode and measurement electrode, on the other hand.

6. The apparatus of claim 1, further including
   means for applying a pressure to the second side of the substrate to controllably blow away particulate that has accumulated on the first side of the substrate.

7. The apparatus of claim 1, wherein the measurement electrode has a composite structure including a measurement conductor, a pair of confinement conductors, one on either side of the measurement conductor, and an insulation layer between each of the confinement conductors and the measurement conductor.

8. The apparatus of claim 7, wherein the confinement conductors and the measurement conductor are grounded.

9. Particulate resistivity measurement apparatus, comprising:
   a hollow cylindrical substrate made of an electrical insulator;
   a pressure controller communicating with the interior of the substrate, the controller including a vacuum source and a pressurization source;
   two interdigitated electrodes spirally wound on the substrate, including
      a measurement electrode, and
      a reference electrode;
   a measurement power supply that applies a measurement voltage between the measurement electrode and the reference electrode; and
   a current measurement meter that measures the current flowing between the measurement electrode and the reference electrode due to the applied measurement voltage.

10. The apparatus of claim 9, wherein the measurement electrode is a compound electrode, including a measurement conductor, a pair of confinement conductors, on each side of the measurement conductor, and an insulation layer between each of the confinements conductors and the measurement conductor.

11. The apparatus of claim 10, wherein the pair of confinement conductors are grounded.

12. The apparatus of claim 9, further including a shield around the substrate.

13. The apparatus of claim 12, further including a collection power supply that applies a collection voltage between the shield, on the one hand, and the reference electrode and measurement electrode, on the other hand.

14. Particulate resistivity measurement apparatus, comprising:
   a cylindrical substrate that is sealed at the ends to permit control of the interior pressure of the substrate, and is made of a porous ceramic;
   a pressure controller communicating with the interior of the substrate, the pressure controller including
      a vacuum source of a pressure below atmospheric,
      a purging source of a pressure above atmospheric, and
      a valve that is controllable to connect the interior of the substrate to either the vacuum source or the purging source;
   a perforated shield around the exterior of the substrate;
   two interdigitated electrodes spirally wound on the substrate, including
      a measurement electrode having a composite structure including a measurement conductor, a pair of confinement conductors, one at a greater cylindrical radius and one at a lesser cylindrical radius than the measurement conductor, and an insulation layer between each of the confinement conductors and the measurement conductor, each of the confinement conductors being at ground potential, and
      a reference electrode;
   a measurement power supply that applies a measurement voltage between the reference electrode and the measurement conductor of the measurement electrode; and
   a current measurement meter that measures the current flowing between the reference electrode and the measurement conductor due to the applied measurement voltage.

15. The apparatus of claim 14, further including a shield around the substrate.

16. The apparatus of claim 15, further including a collection power supply that applies a collection voltage between the shield, on the one hand, and the reference electrode and measurement electrode, on the other hand.

* * * * *